(12) United States Patent
Nigon (10) Patent No.: US 9,381,077 B2
(45) Date of Patent: Jul. 5, 2016

(54) EXTRACTION KIT FOR A FILTER FOR THE VENA CAVA

(75) Inventor: Alain Nigon, Bormes les Mimosas (FR)

(73) Assignee: A.L.N., Ghisonaccia (FR)

( * ) Notice: Subject to any disclaimer, the term of this patent is extended or adjusted under 35 U.S.C. 154(b) by 199 days.

(21) Appl. No.: 13/265,380

(22) PCT Filed: May 5, 2010

(86) PCT No.: PCT/FR2010/050857
§ 371 (c)(1),
(2), (4) Date: Oct. 20, 2011

(87) PCT Pub. No.: WO2010/128249
PCT Pub. Date: Nov. 11, 2010

(65) Prior Publication Data
US 2012/0041473 A1    Feb. 16, 2012

(30) Foreign Application Priority Data
May 6, 2009 (FR) ...................... 09 53017

(51) Int. Cl.
*A61F 2/01* (2006.01)

(52) U.S. Cl.
CPC ........... *A61F 2/013* (2013.01); *A61F 2002/011* (2013.01); *A61F 2230/005* (2013.01)

(58) Field of Classification Search
CPC ... A61F 2/01; A61F 2/013; A61F 2002/0011; A61F 2230/005
USPC .................. 606/114, 127, 138, 200; 600/528
See application file for complete search history.

(56) References Cited

U.S. PATENT DOCUMENTS

| 4,655,219 | A  | * | 4/1987 | Petruzzi ..................... 606/206 |
| 6,036,677 | A  | * | 3/2000 | Javier et al. ................. 604/264 |
| 6,792,979 | B2 | * | 9/2004 | Konya et al. ................. 140/92.1 |
| 8,025,668 | B2 | * | 9/2011 | McCartney ................... 606/106 |
| 2006/0211797 | A1 | | 9/2006 | Tsuji et al. |
| 2006/0211979 | A1 | * | 9/2006 | Smith et al. ................... 604/11 |

(Continued)

FOREIGN PATENT DOCUMENTS

| WO | WO 00/44308   | 8/2000 |
| WO | WO 2005/120627 | 8/2000 |
| WO | WO 00/76422   | 12/2000 |
| WO | WO 01/13984   | 3/2001 |

OTHER PUBLICATIONS

PCT International Search Report received in PCT/FR2010/050857.
(Continued)

*Primary Examiner* — Julie A Szpira
(74) *Attorney, Agent, or Firm* — Vedder Price P.C.; Thomas J. Kowalski; Rebecca G. Rudich (57) ABSTRACT

The invention relates to a withdrawal member for a filter for the vena cava, essentially consisting of a head and shape memory or wrought strands forming a tail, said strands being attached to the head and being located on the same side of the head, said withdrawal member including a rod (7) comprising, at the distal end thereof, a plurality of resilient arms (1, 2, 3, 4, 5, 6) flaring from the rod (7), naturally spaced apart from each other and ending in the form of hooks oriented towards the inside so as to grasp the cap of the filter upon tightening, and including a flexible bent area adjacent to the distal end of the rod (7).

21 Claims, 4 Drawing Sheets

(56) References Cited

U.S. PATENT DOCUMENTS

| | | | |
|---|---|---|---|
| 2006/0247572 A1* | 11/2006 | McCartney | 604/19 |
| 2007/0167974 A1* | 7/2007 | Cully et al. | 606/200 |
| 2007/0265595 A1* | 11/2007 | Miyamoto et al. | 604/528 |
| 2009/0182370 A1* | 7/2009 | Volobuyev et al. | 606/200 |

OTHER PUBLICATIONS

Preliminary Search Report and Written Opinion received in parent Application No. FR 0953017.

International Search Report and Written Opinion received in parent Application No. PCT/FR2010/050857.

* cited by examiner

EXTRACTION KIT FOR A FILTER FOR THE VENA CAVA

RELATED APPLICATIONS

The present application is filed pursuant to 35 U.S.C. §371 as a U.S. National Phase application of International Patent Application No. PCT/FR2010/050857, which was filed on May 5, 2010, claiming the benefit of priority to French Patent Application No. FR 0953017 filed on May 6, 2009. The entire content of each of the aforementioned applications is incorporated herein by reference in its entirety.

The present invention relates to an extraction kit for a filter for the vena cava (also referred to as a "cava filter"), to its use and to kits containing it.

Certain pathologies may cause excessive coagulation of the blood, increasing its tendency to form clots (or thrombi). This then leads to deep vein thrombosis.

A major risk arises in a patient suffering from deep vein thrombosis when a clot is detached from the lower limbs and moves through the inferior vena cava to obstruct one or more pulmonary arteries. Since the lungs are no longer supplied with oxygen, an often fatal pulmonary embolism occurs.

Some patients have formal contraindications against an anticoagulant treatment administered.

Filters for the vena cava are designed to effectively protect such patients in particular against the risks of pulmonary embolism.

A vena cava filter is a mechanical device in the form of an umbrella, which is introduced into a vena cava using a catheter. The filter makes it possible to prevent the migration of clots coming from the veins of the lower limbs.

It may be installed permanently. But in many cases, such as when the risk of pulmonary embolism is acceptable or there is no longer a clinical risk of pulmonary embolism, when the patient no longer needs treatment for deep vein thrombosis, when treatment using anticoagulants is possible, or in the event of a change in position or loss of integrity of the filter, it is necessary to be able to extract it.

EP-A-1 187 578 describes a kit for withdrawing a filter for a blood vessel of the umbrella type formed by a cap used as a retaining sleeve having a plurality of resilient strands naturally spaced apart from each other and ending in hooks directed toward the outside so as to be immobilized on the wall of a vessel, said kit comprising a first catheter, a rod which can be inserted into the internal catheter and having at one of its ends a plurality of resilient arms flaring from the rod, naturally spaced apart from each other and ending in hooks directed toward the inside so as to grip the cap of the filter upon tightening, and optionally a second catheter (external catheter) having a diameter adapted to be slid along the internal catheter and a third catheter having a diameter adapted for introduction into the external catheter, the front end of which is closed and foamed so as to act as a dilator when the assembly consisting of the second and third catheters is being introduced into a vessel.

One complication of using filters is tilting of a filter in the vein. The cap becomes wedged against the wall of the vein. This tilting makes it difficult to withdraw the filter.

US 2006/0211979 describes a variable-flexibility catheter capable of advancing to the treated site with sufficient flexibility through a twisting path but also of having sufficient rigidity to advance through an arterial occlusion. This catheter has a rigidity which can be controlled during use. It comprises a heating device and a fusible binder in thermal contact with the heating device, the rigidifying device being arranged in the sheath. The binder is substantially solid at body temperature and can soften above its transition temperature.

The present application relates to improvements of the member used for gripping the cap of a blood vessel filter of the umbrella type with a view to withdrawing it. For example in EP-A-1 187 578, the member in question is the rod having a plurality of resilient arms at one of its ends. It also relates to simplifications and is thereby simpler than devices which can be actuated using a cable.

The present application therefore relates to a withdrawal member for a filter for the vena cava, essentially consisting of a head and shape memory or shaped strands forming a tail, said strands being fixed to the head and located on the same side of the head, said withdrawal member comprising a rod having at its distal end a plurality of resilient arms flaring from the rod, naturally spaced apart from each other and ending in hooks directed toward the inside (i.e. toward the axis) so as to grip the cap of the filter upon tightening, characterized in that it comprises a flexible bent region in proximity to the distal end of the rod.

In the present application and in what follows, since a vena cava filter is intended to be placed centered in a vein, the positions will be indicated by taking the central axis of a vein as a reference, the vascular wall therefore indicating the outside. The term "without strain" refers to the natural spatial configuration of the object in question. The term "under strain" refers to the spatial configuration of the object in question when it is installed in the functional position in a vessel, or in a catheter, and is therefore subjected to external forces. Conventionally, the term "distal" refers to the part of an object furthest away from the user and "proximal" to that which is closest.

The present withdrawal member does not have variable flexibility. It comprises a bent region of essentially constant flexibility whether at room temperature or at human body temperature (about 37° C.) or a few degrees above human body temperature (for example up to about 55° C., up to about 50° C. or up to about 45° C.). It does not comprise a heating device or fusible binder in thermal contact with the heating device, which are arranged in a sheath, the binder being substantially solid at body temperature and able to soften above its transition temperature.

WO 00/44308 and WO 01/13984 relate to a stent. US 2007/265595 and WO 2005/120627 relate to a catheter which can be actuated using a cable.

Said withdrawal member principally comprises at the tip of its distal end a plurality of resilient arms, then an elongate part of the rod, and on the proximal side a handling piece allowing the operator to hold this end of the withdrawal member in particular between two fingers.

The handling piece preferably comprises a female Luer lock connection (standard threaded Luer cone) on the distal side.

Under preferred implementation conditions of the invention, the flexible bent region is provided at least 4 cm from the distal end of the rod without resilient arms, advantageously from 1 to 3, in particular from 1 to 2, more particularly from 1.5 to 2 cm from said end.

Because of the bent region, the axis of the distal end of the rod forms an angle with respect to the principal axis (the axis of the longest straight line) of the rod. Without strain, the bent region may form an angle of from 110° to 170°, preferably from 120° to 160°, in particular from 130° to 150°, more particularly about 150°.

The length of the bent region may range from 2 to 15, preferably from 2 to 12, in particular from 5 to 11, more particularly from 5 to 10 mm.

The bent region is flexible. This means that without strain the bent region forms an angle other than 180°, but if a conventional catheter for this type of intervention, particularly a 6F, 7F, 8F or 9F catheter, is slid over the distal end of the withdrawal member, the action of the catheter is sufficient to straighten the bent region in order to impart a rectilinear shape to the withdrawal member.

Under other preferred implementation conditions of the invention, the resilient arms are fixed, and in particular crimped, on or in a distal tube constituting a distal part of the rod. Advantageously, the bent region starts at the other end of said distal tube.

This distal tube may have a length of from 9 to 16, preferably from 10 to 15, in particular from 11 to 14, more particularly from 12 to 13 mm.

Under yet other implementation conditions of the invention, the bent region is extended on the proximal side by a second tube (proximal tube).

This proximal tube may have a length of from 9 to 16, preferably from 10 to 15, in particular from 11 to 14, more particularly from 12 to 13 mm.

The distal tube or the proximal tube will have a diameter of from 1 to 4, preferably from 1 to 3, in particular from 1 to 2, more particularly about 2.0 mm.

Depending on the embodiment of the withdrawal member of the invention, the elongate part of the rod is fixed to the proximal tube or to the distal tube or to both. It may for example be adhesively bonded, welded, brazed or in particular crimped. Said elongate part of the rod may be formed by a plurality of strands, or preferably a single strand.

The bent region may, for example, be made of polymeric plastic material. It is advantageously made of metal wire. There may for example be 1, 2, 3, 4 or 5 metal wires. 1 or 2 metal wires, in particular made of stainless steel, particularly having a diameter of about 0.3 mm are preferred. The bent shape of each wire may be imparted before or after attachment to the tubes.

The metal wire or a metal wire may in particular be a narrowing of the rod in order to increase the flexibility at this position, or the rod itself, particularly for a withdrawal member comprising a distal tube but no proximal tube.

The metal wire forming the rod has a diameter of from 0.3 to 0.9, preferably from 0.4 to 0.8, in particular from 0.5 to 0.7, more particularly about 0.5 mm.

Under preferred implementation conditions of the invention, the withdrawal member comprises on the distal side a distal tube and a proximal tube, preferably having the same diameter or similar diameters.

In this case, the flexible bent region advantageously has a diameter equal to that of the distal and proximal tubes. A sheath may then be provided, for example made of polymeric plastic material, in particular enclosing the aforementioned 1, 2, 3, 4 or 5 metal wires in order to constitute with the tubes a region having the same diameter. Thus, when the adapted catheter is advanced over the withdrawal member toward the distal end, there is no risk of the catheter being blocked against the edge of the distal tube.

For this purpose, the proximal ends of the distal and proximal tubes, or of the distal tube, may for example be beveled or rounded or provided with a beveled coating in order to form a chamfer.

The number of resilient arms fixed, and in particular crimped, on or in a tube constituting a distal part of the rod may be from 5 to 8, in particular from 6 to 7, more particularly 6.

Preferably, the distal end of at least two of the resilient arms is longitudinally offset. In particular, the free length of the resilient arms is not equal for all the resilient arms.

The resilient arms are advantageously made of a metal such as phinox, nitinol alloy (NiTi), titanium and in particular stainless steel.

When made of stainless steel, and numbering from 5 to 8 and in particular 6 or 7, they will have a diameter of preferably from 0.2 to 0.6, in particular from 0.3 to 0.5, more particularly about 0.4 mm.

The length of the resilient arms, measured between the hook and the free base of the arm, is advantageously from 1.0 to 5.0, preferably from 1.5 to 4.0, in particular from 1.5 to 3.0, more particularly from 1.9 to 2.2 cm.

The resilient arms ending in hooks directed toward the inside so as to grip the cap of the filter upon tightening. To this end, the distal end of each resilient arm is preferably folded in the shape of an L in order to form an approximately right angle with respect to the length of the arm.

In view of its use, the materials used for manufacturing the withdrawal member are biocompatible and/or bioimplantable metals, composites or polymers.

The present application also relates to a method for manufacturing certain aforementioned withdrawal members, characterized in that a first tube is provided to which a plurality of resilient arms flaring from the rod, naturally spaced apart from each other and ending in hooks directed toward the inside, are axially fixed at one end, preferably by crimping, and 1, 2, 3, 4 or 5 metal wires are axially fixed at the other end, preferably by crimping, these being axially fixed, preferably by crimping, to one end of a second tube in order to form a flexible bent region, and an elongate part of the rod is axially fixed to the other end, preferably by crimping, and if desired a handling piece is provided on the proximal side of said rod, allowing the operator to hold this end of the withdrawal member in particular between two fingers.

The withdrawal members to which the present invention relates have highly beneficial properties. They make it possible to recover vena cava filters axially aligned properly in a vein but furthermore, by virtue of their design, the same withdrawal member makes it easy to recover filters which have tilted in the vein, and to straighten them if necessary. It is also usable equally well for a filter having a simple cap and for and a cap provided with a proximal ring or hook. The particular configuration of the end of the withdrawal member, with a bent region in proximity to the distal end of the rod, means that some of the hooks are naturally placed against the wall of a tube such as a blood vessel, without other intervention, in order to hook the cap of a tilted filter. The flexibility of the bent region allows the withdrawal member to advance to the position of a filter with sufficient flexibility through a twisting path, but the entire withdrawal member has sufficient rigidity to advance for example through an arterial occlusion.

These qualities will be illustrated below in the part describing the figures. They justify the use of the withdrawal members as described above in a method for withdrawing or straightening a vena cava filter installed in a vein.

This is why the present application also relates to a method for withdrawing a vena cava filter installed in a vein, characterized in that a withdrawal member as described above is inserted in the straight position into the vena cava of a patient and the cap of a vena cava filter is gripped, either directly if the filter is axially aligned correctly or after having retracted the catheter holding the withdrawal member in the straight position, in order to curve its distal end.

The present application also relates to a kit (or assembly) comprising
- a withdrawal member as described above,
- an assembly consisting of an internal catheter, preferably 7F, and an external catheter, preferably 9F, having diameters adapted to the withdrawal member, the internal catheter and the external catheter preferably having diameters differing by 2F (for example a 7F internal catheter and a 9F external catheter).

The present application also relates to a kit as described above, furthermore comprising a dilator catheter and optionally a J-shaped guide for reaching the implantation site.

It furthermore relates to one of the aforementioned kits, furthermore containing instructions for using the equipment of the kit.

It also relates to one of the aforementioned kits, furthermore containing a puncture needle.

The withdrawal members and the kits according to the invention may more precisely be used as follows, in the case of an inferior vena cava.

The right jugular vein is punctured using a puncture needle. A J-shaped guide covered with TEFLON® is lowered using a stiffener to 5 cm above the filter to be extracted, while monitoring its progression by radioscopy. The puncture needle is withdrawn. The assembly consisting of the external catheter and the dilator catheter is slid over the J-shaped guide as far as its distal end, while monitoring its progression by radioscopy using a radiopaque ring. The J-shaped guide and the dilator catheter are withdrawn at the same time under frontal and especially profile radioscopy. A wedge is installed between the handling piece of the withdrawal member and the entry of the internal catheter, in order to avoid inadvertently pushing the rod and opening the hooked gripper into the shape of an umbrella. The internal catheter, in which the withdrawal member is installed, is introduced while ensuring the latter is not lowered beyond the intended 5 cm margin, and while continuing to monitor the entire operation by radioscopy. The wedge is then removed and the rod is advanced a little in order to open the hooked gripper. Once the recovery hooks have been opened, they are lowered slowly over the cap of the filter to be recovered. Care is taken that the hooks are placed sufficiently below the cap. If the filter is axially misaligned, the external catheter is retracted a little toward the proximal part of the withdrawal member, which causes the distal end to curve. The cap of the filter to be recovered can thus be gripped better.

At this point in the procedure, the external catheter is slid slowly over the hooks at the end of the rod. Optionally, blocking is carried out by again installing the wedge or a slightly shorter wedge. Still under radioscopy, care is taken that the hooks of the gripper are properly closed under the cap of the filter and properly centered. The external catheter continues to be lowered slowly beyond the cap of the filter, so as to fold its strands inward. Care is taken that the hooks of the filter are properly unhooked from the vascular wall. In a slow movement, the external catheter is pushed along the internal catheter until the gripper and the filter which it has hooked are fully introduced into the external catheter. The assembly consisting of the two catheters with the withdrawal member and the filter is removed. Hemostasis is subsequently ensured at the puncture point.

It will be understood from this that the external catheter can advance beyond the end of the internal catheter.

The preferred implementation conditions of the withdrawal members according to the invention, as described above, also apply to the other subjects of the invention as mentioned above, in particular to the methods for their manufacture, to the kits and the methods of use.

The invention will be understood more clearly by referring to the appended drawings, in which.

Figure 1:
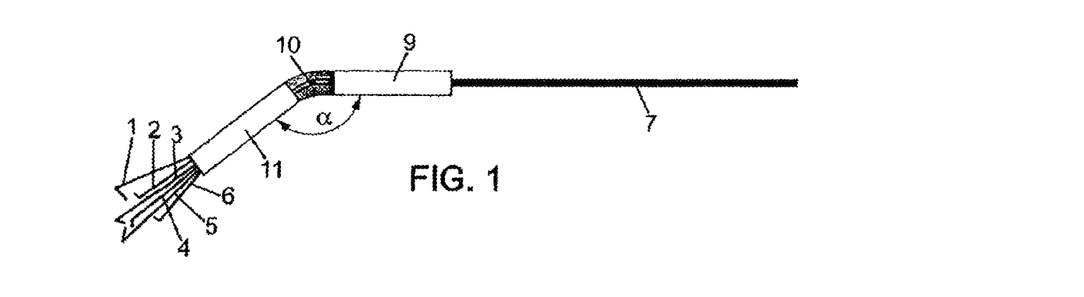
FIG. 1 represents a side view of the distal end of a withdrawal member according to the invention, in partial section level with the bend, without strain.
Figures 3, 4:
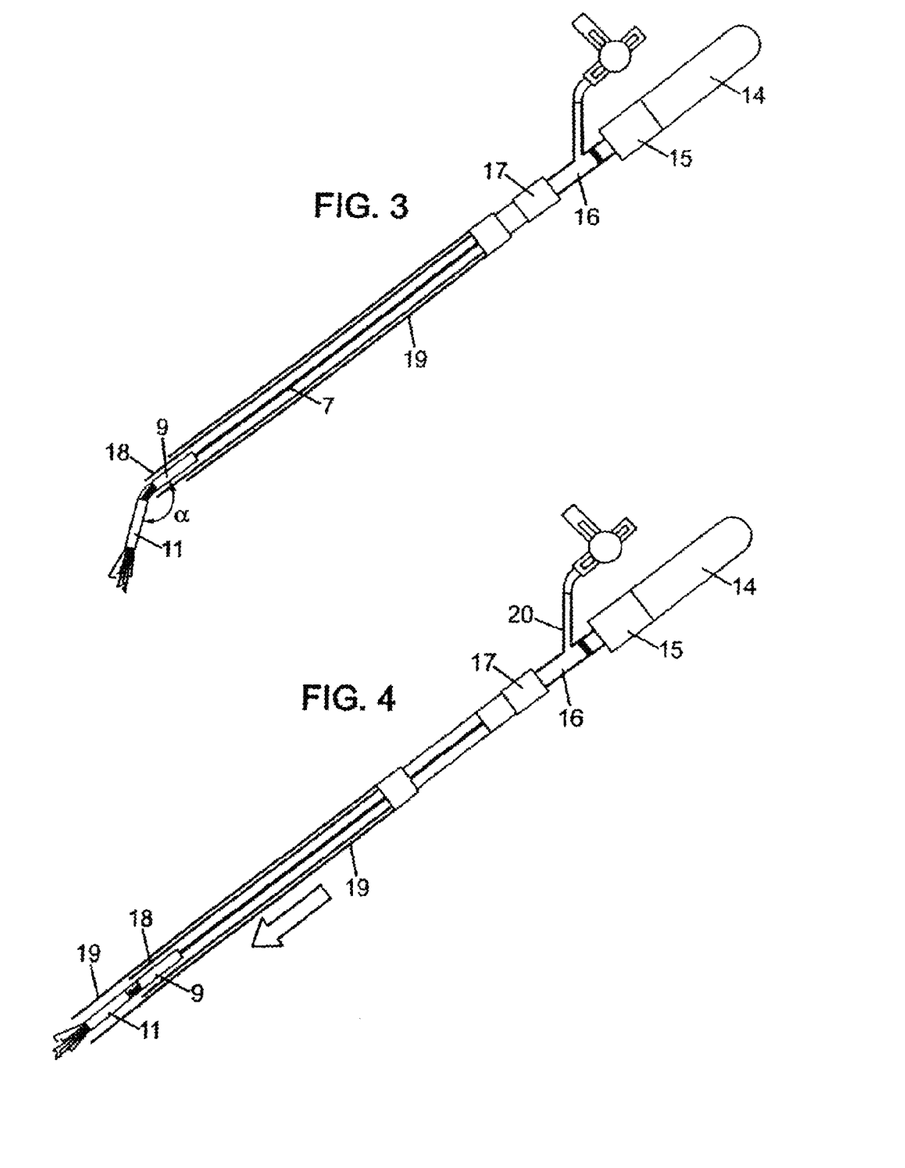
FIG. 3 is a view in lateral elevation and in partial section of a kit using the withdrawal member of the invention.
FIG. 4 also represents a view in lateral elevation and in partial section of a kit using the withdrawal member of the invention.

FIG. 1 shows the distal end of a withdrawal member according to the invention in partial section level with the bend. Such a withdrawal member comprises at the tip of its distal end a plurality of resilient arms 1, 2, 3, 4, 5, 6 then an elongate part of the rod 7 and, on the proximal side, a handling piece 14 which is represented in FIG. 3. Starting from the proximal end, the elongate part of the rod can be seen which is formed here by a single steel strand having a diameter of 0.7 mm. It is crimped into a proximal tube 9 made of steel with a diameter of 2 mm and a length of 12 mm. Two bent steel strands 10 are crimped to the other end of the tube 9, and their other end is crimped into a distal tube 11 also with a diameter of 2 mm and a length of 12 mm. Six resilient arms 1, 2, 3, 4, 5, 6 made of steel wire and having a diameter of 0.4 mm are crimped into the distal part of the distal tube 11. These arms have an overall shape of an L in which the angle formed by the short branch with respect to the long branch is 90°.

These arms are of unequal length. There is one arm with a length of 19.75 mm, one arm with a length of 20.07 mm, one arm with a length of 20.21 mm, one arm with a length of 20.47 mm, one arm with a length of 20.68 mm and one arm with a length of 20.99 mm.

The short branches forming the hook have a length of about 1.9 mm.

The free lengths of the arms (that is to say the length extending from the exit of the distal tube to the most distal part of the arms) are therefore stepped between about 19 and about 21 mm.

The strands 10 are incorporated in a sheath of polymer material having a diameter which is the same as that of the proximal tube 9 and distal tube 11.

Owing to the presence of the bent strands 10, the axis of the distal tube and the axis of the proximal tube form an angle α of about 150° with respect to one another.

Figure 2:
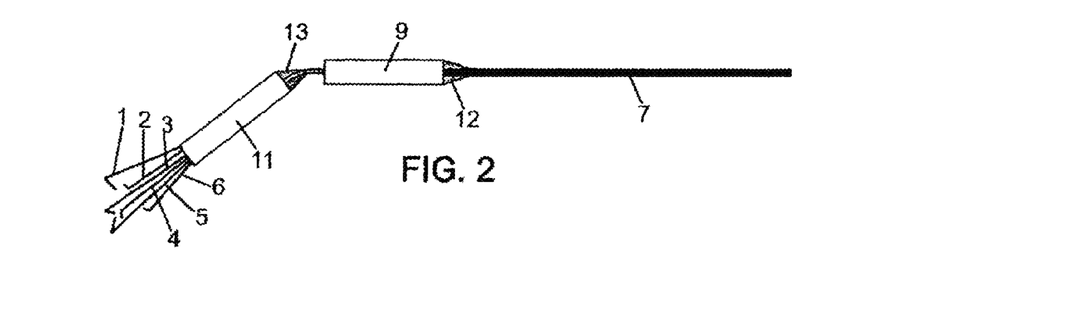
FIG. 2 represents an alternative embodiment of FIG. 1.

FIG. 2 shows a variant of FIG. 1 in which, in order to prevent a catheter from being blocked when it advances toward the distal end by abutting against the edge of one of the tubes, the proximal end of each of these is chamfered in the form of a cone 12, 13. The latter has been formed by chamfering the tubes.

In an alternative embodiment with a chamfer, an attached frustoconical piece made of polymeric plastic has been installed in order to constitute the chamfer.

In another alternative embodiment with a chamfer, only the distal tube 11 has been installed, and it is the rod 7 which penetrates directly into this distal tube 11. In this case, the rod 7 has been narrowed to a diameter of 0.5 mm level with the bend, in order to increase the flexibility here.

In yet another alternative embodiment, a stainless steel wire with a diameter of 0.5 mm has been used to form the rod 7.

FIG. 3 shows, at the center of the arrangement, the withdrawal member according to the invention. At the proximal end of the rod 7, there is a handling piece 14 made of rigid plastic. It is cylindrical and ends on the proximal side in a hemispherical dome and on the distal side in a male Luer lock connection 15. The latter is introduced and blocked on the proximal end of a Y-shaped connector 16, itself provided at its distal end with a male Luer lock connection 17 similar to that of the handle. The cone of the latter connection 17 is introduced into the end of the female Luer lock of the internal catheter 18. A hemostatic valve is provided on the distal part of the main arm of the Y-shaped connector in order to prevent the blood from rising to the handle. A 3-way tap provided with two female Luer locks is connected to the secondary arm 20 of the Y-shaped connector. At the distal exit of this internal catheter 18 (diameter 7F=2.31 mm internal) is the proximal tube 9 of the withdrawal member. Since the distal part of the latter is not subjected to any strain, it is bent at an angle α of about 150°.

FIG. 4 shows the same elements as FIG. 3. However, the external catheter 19 (diameter 9F=3 mm internal) has been moved forward and, owing to its flexibility, the distal end of the withdrawal member has been made straight.

Figure 5:
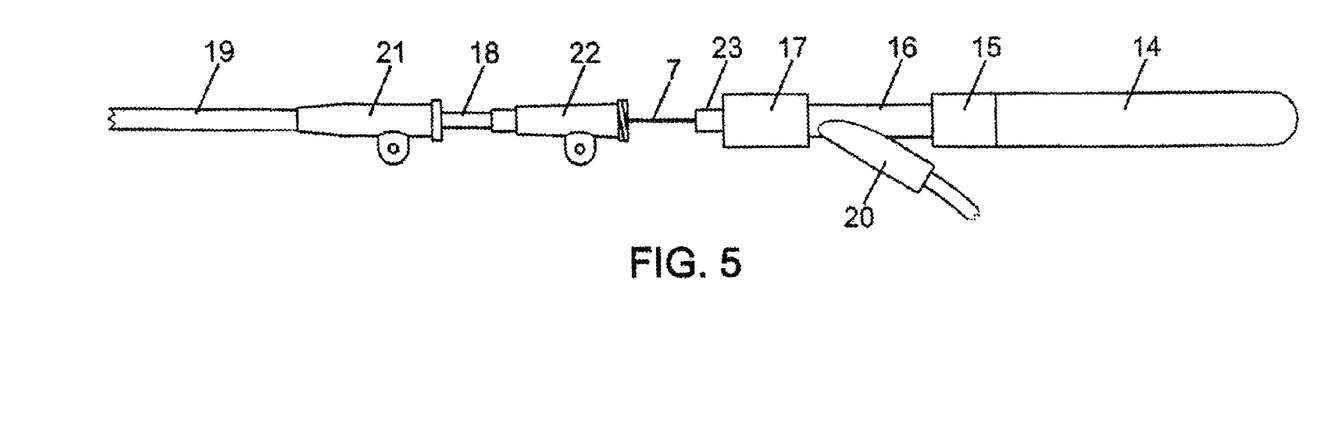
FIG. 5 represents a side view of the proximal end of an improved withdrawal member according to the invention.

FIG. 5 shows, from the proximal end on the right of the drawing, a handling piece 14 made of rigid plastic secured to the rod 7. This handling piece 14 is cylindrical and ends on the distal side in a hemispherical dome and on the distal side in a male Luer lock connection 15. The latter cooperates with a female Luer lock cone of the Y-shaped connector 16. At the other end of the main arm of the Y-shaped connector 16 there is a male Luer lock connection 17, which is similar to that 15 of the handle and the cone 23 of which can be seen. The rod 7 passes through the Y-shaped connector 16 and can slide in the internal catheter 18 (here of 7F diameter) which can itself slide in the external catheter 19 (here of 9F diameter).

The proximal end of the internal catheter 18 has an overmolding 22, of which the proximal aperture is a female Luer cone and the proximal ring permits the blocking (lock). This overmolding 22 is provided with a pierced lug, as is the overmolding 21 with which the proximal end of the external catheter 19 is provided. The proximal aperture of the overmolding 21 is arranged so as to cooperate with the distal end of the overmolding 22.

Figure 6:
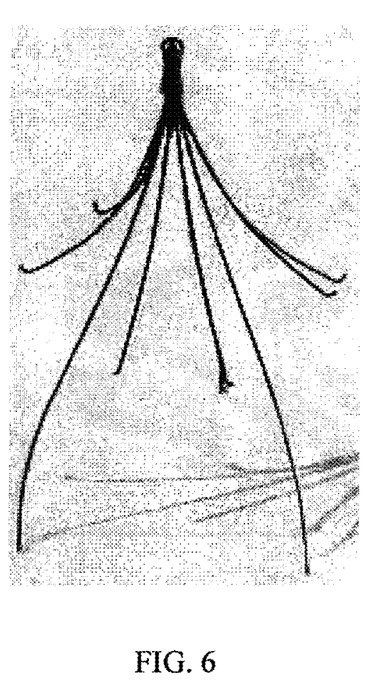
FIG. 6 illustrates an example of a filter having a cap.

FIG. 6 illustrates an example of a filter having a cap. FIG. 6 further illustrates the arms being longitudinally offset.

The invention claimed is:

1. A withdrawal member for a filter for the vena cava, the filter having a cap and shape memory or shaped strands forming a tail, said strands being fixed to the cap and located on the same side of the cap, said withdrawal member comprising side by side and in the following order:
    a rod with a distal end;
    a flexible region;
    a distal tube; and
    a plurality of resilient arms;
    wherein
    (i) the distal tube has a first end and a second end, the first end being the farther from the distal end of the rod and the second end the closer from the distal end of the rod,
    (ii) the plurality of resilient arms flares from the first end of the distal tube, said resilient arms naturally spaced apart from each other and ending in hooks directed inward so as to grip the cap of the filter upon tightening,
    (iii) the flexible region is adjacent the second end of the distal tube and spaced from the plurality of resilient arms by the distal tube; and
    (iv) the flexible region is in a bent position when it is not strained, such that a longitudinal axis of the distal tube and a principal axis of the rod form an angle (α) different front 180°.

2. The withdrawal member recited in claim 1, wherein the flexible bent region is provided at from 1 to 3 cm from the first end of the distal tube.

3. The withdrawal member recited in claim 1, further comprising the distal tube having an axis forming an angle (α) of from 120° to 160° with respect to a principal axis of the rod.

4. The withdrawal member recited in claim 1, wherein the flexible bent region has a length of from 5 to 11 mm.

5. The withdrawal member recited in claim 1, wherein the resilient arms are fixed on or in the distal tube.

6. The withdrawal member recited in claim 5, wherein the flexible bent region is extended on the proximal side by a proximal tube.

7. The withdrawal member recited in claim 6, wherein the distal tube or the proximal tube has a diameter of from 1 to 4 mm.

8. The withdrawal member recited in claim 5, wherein the number of resilient arms fixed on or in the distal tube constituting is from 5 to 8 and lengths of at least two of the resilient arms are unequal.

9. The withdrawal member for a filter for the vena cava of claim 1, wherein the rod comprises a thick portion having a first diameter and a narrow portion having a second diameter, wherein the second diameter is less than the first diameter, and wherein the flexible bent region comprises the narrow portion of the rod.

10. A withdrawal member for a filter for the vena cava, comprising side by side and in the following order:
    a proximal tube having a proximal longitudinal axis and a proximal tube diameter;
    a flexible region;
    a distal tube;
    a plurality of resilient arms;
    wherein the proximal tube has a proximal longitudinal axis and a proximal tube diameter;
    wherein the distal tube has a distal longitudinal axis a distal tube diameter;
    wherein the flexible region extends between the proximal tube and the distal tube, and is in a bent position when the flexible region is unstrained such that the proximal longitudinal axis and the distal longitudinal axis form a predetermined resting angle different from 180; and
    wherein the plurality of resilient arms extends from an end of the distal tube and separated from the flexible region by the distal tube.

11. The withdrawal member for a filter for the vena cava of claim 10, wherein the flexible bent region has a diameter substantially equal to the proximal tube diameter.

12. The withdrawal member for a filter for the vena cava of claim 10, wherein the flexible bent region has a diameter substantially equal to the distal tube diameter.

13. The withdrawal member for a filter for the vena cava of claim 10, wherein the predetermined resting angle is about 150 degrees.

14. A withdrawal member for a filter for the vena cava comprising:
    a proximal tube having a proximal longitudinal axis and a proximal tube diameter;
    a distal tube having a distal longitudinal axis and a distal tube diameter;

a flexible bent region extending between the proximal tube and the distal tube, wherein the proximal longitudinal axis and the distal longitudinal axis form a predetermined resting angle; and a plurality of resilient arms extending from an end of the distal tube and separated from the flexible bent region by a length of the distal tube, wherein the flexible bent region comprises bent steel strands fixed to the distal tube.

15. The withdrawal member for a filter for the vena cava of claim 14, the flexible bent region further comprising a polymer sheath encompassing the bent steel strands and having a diameter substantially the same as at least one of the proximal tube diameter and the distal tube diameter.

16. The withdrawal member for a filter for the vena cava of claim 10, wherein the resilient arms are fixed with respect to the distal tube.

17. The withdrawal member for a filter for the vena cava of claim 10, wherein each of the resilient arms comprise a long branch and a short branch, wherein each short branch forms a predetermined angle with respect to the respective long branch and wherein respective long branches of at least two of said resilient arms have unequal lengths.

18. The withdrawal member for a filter for the vena cava of claim 10, wherein the resilient arms each comprise a long branch and a short branch, wherein an angle formed by the short branch with respect to the long branch is about 90 degrees.

19. The withdrawal member for a filter for the vena of claim 10, wherein the resilient arms extend from a distal end of the distal tube and the flexible bent region extends from a proximal end of the distal tube and wherein the flexible bent region extends from a distal end of the proximal tube, further comprising:

a rod extending from a proximal end of the proximal tube.

20. A withdrawal member for as filter for the vena cava comprising:

a proximal tube having a proximal longitudinal axis and a proximal tube diameter;

a distal tube having a distal longitudinal axis and a distal tube diameter;

a flexible bent region extending between the proximal tube and the distal tube, wherein the proximal longitudinal axis and the distal longitudinal axis form a predetermined resting angle; and a plurality of resilient arms extending from an end of the distal tube and separated from the flexible bent region by a length of the distal tube;

wherein the resilient arms extend from a distal end of the distal tube and the flexible bent region extends from a proximal end of the distal tube and wherein the flexible bent region extends from a distal end of the proximal tube, further comprising;

a rod extending from a proximal end of the proximal tube;

further comprising the proximal end of the distal tube and the proximal end of the proximal tube each having a chamfer.

21. The withdrawal member for a filter for the vena cava of claim 20, wherein the chamfer comprises a separate polymeric plastic piece having a frustoconical shape.

* * * * *